United States Patent [19]

Nakamura et al.

[11] 4,259,448
[45] Mar. 31, 1981

[54] PROTEIN ADSORBENT AND PROCESS FOR THE PURIFICATION OF UROKINASE

[75] Inventors: Hiroaki Nakamura, Kawasaki; Izumi Kumita, Ohiso; Yoshiji Sugita, Hiratsuka; Hiedo Takagi, Ohiso, all of Japan

[73] Assignee: Nippon Soda Company, Ltd., Ohtemachi, Japan

[21] Appl. No.: 83,308

[22] Filed: Oct. 10, 1979

Related U.S. Application Data

[63] Continuation-in-part of Ser. No. 866,794, Jan. 3, 1978.

[51] Int. Cl.³ .............................................. C12N 9/72
[52] U.S. Cl. ....................................... 435/215; 536/1
[58] Field of Search ........................................ 435/215

[56] References Cited

U.S. PATENT DOCUMENTS

| | | | |
|---|---|---|---|
| 3,746,622 | 7/1973 | Nishikawa et al. | 435/188 |
| 4,066,506 | 1/1978 | Johnson et al. | 435/215 |
| 4,165,258 | 8/1979 | Pye et al. | 435/215 |

OTHER PUBLICATIONS

Holmberg et al., Biochimica and Biophysica Acta, vol. 445, No. 1, pp. 215–222 (1976).

*Primary Examiner*—Lionel M. Shapiro
*Attorney, Agent, or Firm*—George B. Oujevolk

[57] ABSTRACT

A novel protein adsorbent having a group of the general formula

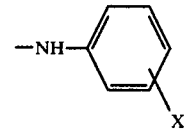

wherein X is hydrogen, halogen, amino, lower alkyl or lower alkoxycarbonyl as a ligand, is useful for the purification of urokinase by hydrophobic chromatography, particularly for the removal of such kind of pyrogen that is scarcely removed by affinity chromatography on the ordinal adsorbent of urokinase.

2 Claims, No Drawings

PROTEIN ADSORBENT AND PROCESS FOR THE PURIFICATION OF UROKINASE

This application is a continuation-in-part of U.S. Patent application Ser. No. 866,794, filed Jan. 3, 1978.

DETAILED DESCRIPTION OF THE INVENTION

This invention relates to a protein adsorbent and purification of urokinase from human urine by hydrophobic chromatography on the protein adsorbent.

Urokinase is a plasminogen-activating enzyme found in a trace amount in human urine and is used as an effective thrombolytic agent and a drug used together with anticancer. High purity of urokinase is required because these drugs are used by an intravenous injection.

Recently, affinity chromatography has begun to be used as a method for the purification of human urokinase and various urokinase adsorbents for the affinity chromatography are known, for example, a urokinase adsorbent having amidine or guanidine group as a ligand (U.S. Pat. No. 3,746,622). These known urokinase adsorbents are effective for the purification of human urokinase by affinity chromatography with respect to the removal of proteins and a considerable amount of pyrogen contained in human urokinase as impurities, however, a certain kind of pyrogen, which of amount is small, can not be removed by the affinity chromatography on the known urokinase adsorbents, because that kind of pyrogen acts as in the same manner as urokinase on the urokinase adsorbents at adsorbing step as well as eluting step.

It is an object of the invention to provide a novel adsorbent which does not adsorb urokinase but adsorbs impure proteins and pyrogen. It is another object of the invention to provide a simple method for the purification of human urokinase.

The inventors found that the material using a compound of the general formula [I]

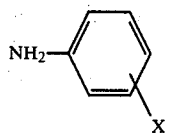

wherein X is hydrogen, halogen, amino, lower alkyl or lower alkoxycarbonyl as a ligand compound, have a property not to adsorb urokinase and to adsorb pyrogen and proteins contained in crude human urokinase as impurities, when it is used as an adsorbent for hydrophobic chromatography.

Affinity chromatography or hydrophobic chromatography has been usually carried out on an adsorbent which adsorbs a desired compound and does not adsorb impurities, and no method for the purification or urokinase by hydrophobic chromatography has been known.

The protein adsorbent of this invention is the material which comprises an water insoluble carrier and the compounds indicated by the formula [I].

The compound of the formula [I] is coupled to the carrier directly or through spacers. Usually, spacer is first coupled to the carrier, namely, the group of the formula [II] or [III]

—NH(CH₂)ₗNHCOCH₂CH₂COOH      [II]

—NH(CH₂)ₗCOOH      [III]

in which l is an integer of from 3 to 10, is bound to the carrier. The compound of the formula [I] is coupled to the modified carrier. Namely, the protein adsorbent of the invention may be shown as follows:

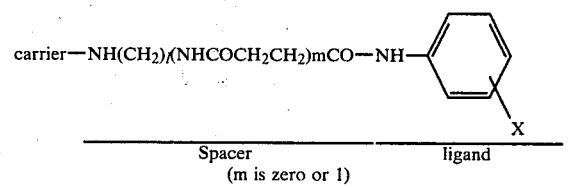

As the water insoluble carrier, any material having the functional group to which the terminal amino group of the spacer or the ligand compound can be coupled may be used. Suitable carriers are polysaccharides such as agarose, crosslinked dextran, celluloses and agar-agars, polymer such as acrylamide, and glass powder. Agarose is the most preferable carrier. Agarose or modified agarose, for example, agarose to which hexamethylenediamine is coupled, is sold on the market as a carrier for affinity chromatography. Those products on the market can be used in this invention.

The adsorbent of the invention can be constructed by the known process. For example, in the case that the carrier is agarose, first, the agarose is activated with cyanogen bromide and sequently coupled to diaminoalkane and then succinic anhydride, or coupled to amino acid to produce a modified carrier having a group of formula [II] or [III]. The ligand precurser, the compound of formula [I], is then coupled to the modified agarose in the presence of water soluble carbodimides to form the adsorbent of the invention.

Similar method is disclosed in the literature, "Method in Enzymology, 34, 451-455 (1974)."

When carrying out the hydrophobic chromatography, the solution containing the crude urokinase which is prepared from human urine in a usual simple method, is adjusted to the salt concentration of 0.2 to 2 M, preferably 0.2 to 1 M. The solution is then made to flow through the hydrophobic column packed with the protein adsorbent of the invention.

Fresh human urine may be applied to the adsorbent, however, human urine is usually pretreated in a usual method before it is applied to the hydrophobic column. For example, the foam made by stirring human urine is collected and a defoaming agent is added thereto and the solution is adjusted to pH 8.5-9 to form precipitates. The resulting supernatant solution may be applied to the hydrophobic column. Further, the supernatant solution may be treated, namely, a weakly acidified supernatant solution is contacted with diatomaceous earth to recover the crude urokinase in a usual method. The resulting crude urokinase is dissolved in water and the solution may be applied to the hydrophobic column of this invention.

The pH is not critical when carring our the hydrophobic chromatography, however, the pH is usually adjusted to pH 5.5-10, preferably 6-8.5 at which pH urokinase is stable against inactivation.

Purified urokinase can be obtained by treating the effluent from the hydrophobic column in a usual method, namely by lyophilization after desalting.

The purification process of this invention is very simple because the purification can be attained by only passing a crude urokinase solution through the hydrophobic column while the affinity chromatography requires adsorbing step and eluting step.

Although only the process of this invention may attain the purification of urokinase, further purification can be easily attained by treating the effluent from the hydrophobic column with known affinity chromatography, since the effluent does not contain such a kind of pyrogen that is scarecely removed by the affinity chromatography on the known urokinase adsorbent.

To further illustrate this invention, and not by way of limitation, the following examples are given.

EXAMPLE 1

To a suspension of 100 ml of Sepharose 4B (product by Pharmacia Fine Chemicals) in 100 ml of water were added 200 ml of 5% aqueous solution of CNBr with stirring. The reaction was allowed to proceed for 10 minutes at 20° C. while adding NaOH aqueous solution to keep the reaction mixture at pH 11. The reaction mixture was then filtered and the activated Sepharose was washed with 1.5 l of 0.1 M $NaHCO_3$. The activated Sepharose was rapidly suspended in the solution of ε-aminocaproic acid which was prepared by dissolving 1.31 g of ε-aminocaproic acid in 100 ml of 0.1 M $NaHCO_3$ and then adjusting to pH 9.5, and was reacted for 16 hours at 4° C. The reaction product was washed with 1 l of 0.5 M NaCl and then 1 l of distilled water to obtain the modified Sepharose, Sepharose-ε-aminocaproic acid. To this modified Sepharose were added n-butyl-p-aminobenzoate solution which was prepared by dissolving 500 mg of the compound in 250 ml of 40% dimethyl formamide and adjusting to pH 4.7. To the mixture were added 3 g of 1-ethyl-3-(3-dimethylaminopropyl)carbodiimide HCl dissolved in 5 ml of water and the reaction was allowed to proceed for 18 hours at the room temperature. During the first one hour of the reaction the pH was maintained at pH 4.8 by adding 1 N HCl. The reaction mixture was filtered and washed with 500 ml of 0.5 M NaCl and then 500 ml of distilled water to obtain the protein adsorbent (No. 1) of the invention.

EXAMPLE 2

To a suspension of 20 ml AH-Sepharose (product by Farmacia Fine Chemicals) in 20 ml of water were added 2 g of succinic anhydride and the reaction was allowed to proceed at 4° C., maintaining the pH at 6 by adding aqueous NaOH. After the change of the pH disappeared, the reaction was further continued for 5 hours. The reaction mixture was filtered and washed with 1 l of water to obtain the modified Sepharose, succinyl AH-Sepharose. To a suspension of the resulting succinyl AH-Sepharose in 50 ml of 40% aqueous solution of dimethyl formamide were added 25 mg of aniline and the pH was adjusted to 4.8. To the mixture were added 80 mg of 1-ethyl-3-(3-dimethyl-aminopropyl)-carbodiimide dissolbed in 2 ml of water and the reaction was allowed to proceed at room temperature for 18 hours. During the first one hour of the reaction the pH was maintained at 4.8 by adding 1 N HCl. The reaction mixture was filtered and washed with 500 ml of 0.5 M NaCl and then 500 ml of distilled water to obtain the protein adsorbent (No. 4) of the invention.

Examples of the protein adsorbents produced in Examples 1 and 2, or produced in the same manner as in those Examples are listed as follows: In the following, "Aga" indicates agarose.

No. 1: Aga-$NH(CH_2)_5CONHC_6H_4$-p-$COOC_4H_7{}^n$
No. 2: Aga-$NH(CH_2)_5CONHC_6H_4$-p-Cl
No. 3: Aga-$NH(CH_2)_5CONHC_6H_4$-m-Cl
No. 4: Aga-$NH(CH_2)_6NHCOCH_2CH_2CONHC_6H_5$
No. 5: Aga-$NH(CH_2)_6NHCOCH_2CH_2CONHC_6H_4$-o-$CH_3$
No. 6: Aga-$NH(CH_2)_6NHCOCH_2CH_2CONHC_6H_4$-p-$NH_2$
No. 7: Aga-$NH(CH_2)_6NHCOCH_2CH_2CONHC_6H_4$-m-$NH_2$

Pre-treatment of human urine

Fresh human urine was stirred and the resulting foam was separated. A defoaming agent was added to the foam and adjusted to pH 8.7 by adding aqueous NaOH. The resulting precipitate was removed to obtain the supernatant solution containing crude urokinase. The crude urokinase solution was adjusted to pH 5.5 by adding aqueous HCl and it was contacted with diatomaceous earth to adsorb urokinase was eluted with 3% aqueous solution of $NH_3$ after washing the diatomaceous earth with water to remove impurities. The eluate was ultrafiltrated by hollow-fiber and lyophilized to obtain the powder of crude urokinase, which of specific activity was 5,000 international units/mg protein. The crude urokinase was purified in the following Examples.

EXAMPLE 3

20 ml of crude urokinase solution which was prepared by dissolving the crude urokinase (250,000 international units) in 0.3 M NaCl in 0.1 M phosphate buffer (pH 7.5), was passed through the hydrophobic column packed with 10 ml of adsorbent of the invention. The column was washed with 100 ml of 0.3 M NaCl in 0.1 M phosphate buffer. The effluent from the column was desalted, concentrated and lyophylized in a usual way to obtain purified urokinase. The results are as follows:

| Protein Adsorbent No. | Purified Urokinase | |
| --- | --- | --- |
| | Specific Activity (i.u./mg protein) | yield (%) |
| 1 | 34,000 | 89 |
| 2 | 29,000 | 85 |
| 3 | 31,000 | 90 |
| 4 | 31,000 | 90 |
| 5 | 27,000 | 92 |
| 6 | 24,000 | 89 |
| 7 | 29,000 | 87 |

EXAMPLE 4

A column (hydrophobic column) of 2.5 cm diameter packed with 100 ml of the protein adsorbent No. 4 was connected with another column (affinity column) of 2.5 cm diameter packed with 100 ml of the following adsorbent for urokinase in series.

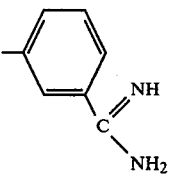

Through the hydrophobic column was passed a crude urokinase solution containing 10 million international units of urokinase which was prepared by dissolving the crude urokinase in 500 ml of 0.2 M NaCl in 0.1 M phosphate buffer (pH 7.4). The hydrophobic column was washed with 2 l of 0.2 M NaCl in 0.1 M phosphate buffer (pH 7.4). The effluent from the hydrophobic column was successively passed through the affinity column. Then the hydrophobic column was removed and after washing the affinity column with 1 l of 0.1 M NaCl, the urokinase adsorbed by the affinity column was eluted with 0.1 M acetate buffer (pH 5.0).

The fraction containing urokinase was ultrafiltrated, dialyzed and lyophilized to obtain 8.56 million international units of urokinase with a specific activity of 82,700 international units/mg protein. Pyrogen test was applied to the purified urokinase according to the Japanese Pharmacopeia. The result was negative at a dosage of 8,000 international units/kg.

EXAMPLE 5

A crude urokinase solution containing 10 million international units of urokinase, which was prepared by dissolving the crude urokinase in 500 ml of 0.4 M NaCl in 0.1 M phosphate buffer (pH 7.0), was treated in the same way as in Example 4 except that the protein adsorbent No. 1 was used instead of No. 4. Thus, 7.8 million international units of purified urokinase with a specific activity of 95,200 international units/mg. protein was obtained. Pyrogen test of the purified urokinase was negative at a dosage of 8,000 international units/kg.

COMPARATIVE EXAMPLE 25 ml of crude urokinase solution containing 500,000 international units of urokinase, which was prepared by dissolving the crude urokinase in 0.3 M NaCl in 0.1 M phosphate buffer (pH 7.5), was passed through the affinity column packed with 20 ml of the same adsorbent for urokinase as in Example 4. After washing the column with 200 ml of 0.1 M NaCl, adsorbed urokinase was eluted with 0.1 M acetate buffer (pH 5.0). The fraction containing urokinase was treated as in Example 4 to obtain purified urokinase with a specific activity of 35,000 international units/mg protein by a yield of 86%. Pyrogen test of the urokinase was positive at a dosage of 2,000 international units/kg.

We claim:

1. A process for the purification of urokinase which comprises passing a solution containing crude urokinase through a column packed with a protein adsorbent comprising a water insoluble carrier and a ligand, said ligand having the formula

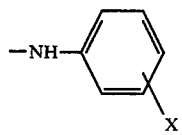

wherein X is selected from the group consisting of hydrogen, halogen, amino, lower alkyl and lower alkoxycarbonyl.

2. A process according to claim 1, wherein a salt concentration in the solution containing crude urokinase is in the range of 0.2 to 2 M.

* * * * *